United States Patent
Novak

(10) Patent No.: US 9,402,716 B2
(45) Date of Patent: Aug. 2, 2016

(54) INTRAOCULAR LENS INSERTER AND SYSTEM AND METHOD REGARDING SAME

(71) Applicant: Abbott Medical Optics Inc., Santa Ana, CA (US)

(72) Inventor: Curt A Novak, Corona, CA (US)

(73) Assignee: ABBOTT MEDICAL OPTICS INC., Santa Ana, CA (US)

(*) Notice: Subject to any disclaimer, the term of this patent is extended or adjusted under 35 U.S.C. 154(b) by 392 days.

(21) Appl. No.: 13/840,797

(22) Filed: Mar. 15, 2013

(65) Prior Publication Data
US 2014/0276898 A1    Sep. 18, 2014

(51) Int. Cl.
  *A61F 9/00* (2006.01)
  *A61F 2/16* (2006.01)
  *A61M 5/20* (2006.01)

(52) U.S. Cl.
  CPC .............. *A61F 2/167* (2013.01); *A61F 2/1672* (2013.01); *A61F 2/1678* (2013.01); *A61M 5/2053* (2013.01)

(58) Field of Classification Search
  CPC ..... A61F 2/1672; A61F 2/167; A61F 2/1678; A61M 5/2053
  See application file for complete search history.

(56) References Cited

U.S. PATENT DOCUMENTS

| 4,613,326 | A  | * | 9/1986  | Szwarc          | A61M 5/284 604/218 |
| 6,406,455 | B1 |   | 6/2002  | Willis et al.   |                    |
| 6,740,062 | B2 | * | 5/2004  | Hjertman        | A61M 5/30 604/131  |
| 2008/0255579 | A1 |   | 10/2008 | Wollenhaupt et al. |                |
| 2009/0292293 | A1 |   | 11/2009 | Bogaert et al.     |                |
| 2012/0289970 | A1 |   | 11/2012 | Pynson             |                |
| 2013/0012956 | A1 |   | 1/2013  | Mirlay             |                |
| 2013/0096428 | A1 | * | 4/2013  | Gillies            | A61M 25/065 600/434 |

FOREIGN PATENT DOCUMENTS

EP    0937443 A2    8/1999

OTHER PUBLICATIONS

International Search Report and Written Opinion for Application No. PCT/US2014/018563 mailed on May 22, 2014, 15 pages.

* cited by examiner

*Primary Examiner* — Robert Lynch
(74) *Attorney, Agent, or Firm* — Abbott Medical Optics Inc.

(57) ABSTRACT

The present inserter, system and method suitable for inserting the IOL may include a lumen having an outer wall and an inner wall, the inner wall including at least one hollowed portion; a plunger for advancing along the lumen, the plunger having a plunger shaft extending into the open proximal end and terminating at a distal plunger end; a reservoir within the lumen between the distal plunger end and the distal insertion tip, the reservoir having an opening that is misaligned with the at least one hollowed portion prior to advancing of the plunger, and that is aligned with the at least one hollowed portion during advancing of the plunger; and a viscous fluid within the lumen, wherein the viscous fluid flows along a bypass formed of the at least one hollowed portion and the opening and into said reservoir, thereby decreasing an inserting displacement force effected at the distal insertion tip from a plunger displacement force applied to said plunger.

20 Claims, 3 Drawing Sheets

INTRAOCULAR LENS INSERTER AND SYSTEM AND METHOD REGARDING SAME

BACKGROUND OF THE INVENTION

1. Field of the Invention

The present invention relates to surgical devices, such as ophthalmic surgical devices, and, more particularly relates to a device, system and method for inserting an intraocular lens (IOL) into an eye.

2. Description of the Background

An IOL is an artificial lens implanted to replace or supplement the natural crystalline lens of an eye due to poor or non-functionality of the natural lens. For example, such poor or non-functionality may occur when the natural lens develops cataracts or is otherwise diseased, by way of non-limiting example, and in such cases the natural lens may be removed from the eye and replaced by an IOL. Such poor or non-functionality may also occur due to refractive errors of the eye, and, for such refractive errors, the natural lens may remain in the eye together with an implanted IOL in order to provide optimal vision.

An IOL may be implanted in the posterior chamber or anterior chamber of the eye. IOLs may be provided in a variety of configurations, for a variety of purposes, and formed of any of numerous available materials. IOLs often include an optic, which typically includes an optically clear lens, and preferably at least one flexible fixation member, or haptic, which extends from the optic and becomes affixed in the eye to secure the IOL in position. For example, common IOLs include open-looped haptics, which include a three-piece IOL having an optic and two haptics attached to and extending from the optic, and a one-piece IOL in which the optic and haptics are integrally formed, and closed looped haptic IOLs. Further, in a plate haptic IOL, the haptics are configured as a flat plate extending from opposite sides of the optic. An IOL may be formed from, by way of non-limiting PMMA, silicone, hydrogels, silicone hydrogels, and combinations thereof.

There exists a number of instruments and methods for implanting an IOL. For example, surgical forceps having opposing blades may be used to grasp the IOL and insert it through an incision. However, this method is deemed relatively crude, and thus, ever more commonly, sophisticated IOL inserter devices are in use. IOL inserter devices offer increased control when inserting the IOL, and decreased need for larger incisions due to reduced diameter insertion tips. It goes without saying that smaller incision sizes, on the order of or less than about 3 mm, allow for reduced post-surgical healing time and fewer complications. However, despite these significant advantages provided by modern IOL inserter devices, lack of sufficient control, particularly at the very point of IOL insertion, still often causes the IOL to "pop" from the inserter device, thereby causing misplacement of the IOL, particularly in view of the decreased maneuverability granted a surgeon due to the decreased incision size typical in IOL inserter device environments.

Further, because IOLs are delicate, great care must be taken in properly handling and precisely inserting an IOL. As referenced, due largely to smaller incision sizes, IOLs are generally folded prior to insertion, and are to assume the correct shape for optimal performance following proper insertion. As such, smooth passage of the IOL from the inserter device to the proper in-situ location is highly desirable to allow for the decompression of the IOL in-situ for optimal performance. Moreover, insertion of the IOL in such a manner so as not to damage the delicate IOL is also highly desirable. A misplaced, improperly oriented, or damaged IOL will likely require manipulation in-situ or removal of the inserted IOL and subsequent insertion of a replacement IOL. This may lead to surrounding tissue damage, or, worse yet, a secondary surgery. For these and other reasons, the aforementioned "popping" of the IOL from the inserter device, due to a lack of control over the inserter at the very point of insertion, is a very detrimental and disadvantageous occurrence.

Therefore, an IOL inserter that permits easy passage of the IOL therethrough, with a great degree of control at the insertion point, and that inserts the IOL into the eye in a predictable and repeatable orientation and manner, would be highly advantageous. Ideally, such an IOL inserter would avoid expulsion from the IOL inserter too quickly, in the wrong location, in the wrong orientation, or in an otherwise unexpected manner (i.e., "popping"), thereby avoiding the need to manipulate the IOL after insertion or to perform a secondary surgery.

In a typical IOL inserter device, a syringe-style plunger is used. The IOL is generally loaded into a closed chamber in a portion of a tapered lumen, i.e., at the lumen portion below the plunger base and toward the inserting tip. At the time of insertion, the plunger is actuated downward through the lumen toward the inserting tip of the IOL inserter, i.e., the plunger forces the IOL through the narrowing lumen toward the tip, thereby increasing the compression on the IOL, and hence the counter-pressure on the plunger. The injecting tip of the lumen is typically sized for insertion into the small surgical incision in the eye, which, as stated above, is presently preferred to be about 3 mm or less. Eventually, the displacement stemming from actuation of the plunger is sufficient to expel the IOL from the inserting tip into the eye, and the IOL unfolds, or decompresses, in-situ. Accordingly, at the point of insertion, the IOL has been compressed to at least the sub 3 mm size of the inserting tip, with a correspondent counter-pressure having built at the point of injection due to the increased compression.

The aforementioned counter-pressure to the actuation of the plunger is what frequently causes the "popping" of the IOL into the eye. As such, refined control of the displacement force at the point of insertion is of the utmost importance to prevent damage to the IOL, or misplacement or improper orientation of the IOL, due to this "popping." However, in spite of the urgent need to remedy the issue of "popping" of the IOL from the inserting tip, this problem remains largely unaddressed in the known art.

Therefore, the need exists for an IOL inserter device, system and method that provides for insertion of an IOL into an eye in a predictable and repeatable orientation and manner, and that accordingly remedies counter-pressure at the point of IOL insertion.

SUMMARY OF THE INVENTION

The present invention is and includes an IOL inserter, and a system and a method regarding same. The inserter and system suitable for inserting the IOL may include a lumen having an open proximal end and a distal insertion tip and a longitudinal passageway extending therebetween, and having an outer wall and an inner wall, the inner wall including at least one hollowed portion; a plunger for advancing along the longitudinal passageway, the plunger having a plunger shaft extending into the open proximal end and terminating at a distal plunger end; a reservoir within the longitudinal passageway between the distal plunger end and the distal insertion tip, the reservoir having an opening that is misaligned with the at least one hollowed portion prior to advancing of the plunger, and that is aligned with the at least one hollowed portion during advancing of the plunger; and a viscous fluid within the longitudinal passageway and at least partially between the distal plunger end and said reservoir, wherein the viscous fluid flows through a bypass formed between the primary chamber and secondary reservoir chamber hollowed portion and the opening and into said reservoir, thereby decreasing an inserting displacement force effected at the distal insertion tip from a plunger displacement force applied to said plunger.

The method of providing for insertion of an IOL may include providing a lumen having inserted therein a plunger, and further having therein a viscous fluid in fluid communication with a distal end of the plunger and with a reservoir; upon an advanced actuation of the plunger, providing a bypass pathway for the viscous fluid such that a displacement at a distal end of the reservoir is non-linear with the actuation of the plunger; and providing for the insertion of an IOL upon at least near-completion of the actuation of the plunger.

Accordingly, disclosed herein is an IOL inserter device, system and method that provides for insertion of an IOL into an eye in a predictable and repeatable orientation and manner, and that accordingly remedies counter-pressure at the point of IOL insertion.

DESCRIPTION OF THE DRAWINGS

The accompanying drawings are included to provide a further understanding of the invention, and are incorporated in and constitute a part of this specification. The drawings illustrate disclosed embodiments and/or aspects and, together with the description, serve to explain the principles of the invention, the scope of which is determined by the claims.

In the drawings, like numerals represent like elements, and.

DETAILED DESCRIPTION

It is to be understood that the figures and descriptions of the present invention have been simplified to illustrate elements that are relevant for a clear understanding of the present invention, while eliminating, for the purpose of clarity, many other elements found in typical surgical, and particularly optical surgical, apparatuses, systems, and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

In short, the present invention may provide an improved and refined IOL insertion apparatus, system and method by providing a reservoir integral to the injector and contained within the inserter's lumen. A bypass pathway, with or without a control valve, may allow a viscous fluid to escape the transfer chamber and thus impart a reduction in displacement at the inserter tip as the plunger is further compressed. As such, the present invention may provide a hydraulically-actuated IOL inserter device that has a reduction in insertion pressure as the plunger stem is compressed.

More particularly, the present invention is directed at least to IOL inserters having a tubular lumen with an inner wall that defines a narrowing, longitudinal passageway from a proximal end to a distal injecting tip of the inserter, and a plunger component which telescopes into the open proximal end of the tubular body. Further, within the tubular lumen is included a reservoir that may have therein a float, wherein a pathway for viscous fluid exists from an opening in the reservoir through an aligned hollowed portion of the inner wall of the lumen. The viscous fluid may reside within the tubular lumen from the plunger base to the topmost portion of the reservoir, such that, upon a downward actuation of the plunger, the viscous fluid is forced against the topmost portion of the reservoir until the opening in the reservoir aligns with the hollowed inner wall portion of the lumen, at which time the viscous fluid will follow the aforementioned viscous fluid bypass pathway, filling the reservoir and moving the float, if the float is mobile, or filling the reservoir to the float point, if the float is set. Thereby, the displacement pressure asserted by the plunger stroke is decreased as the plunger stroke nears the injection point, affording refined control of the plunger stroke at the point of injection.

Figure 1:
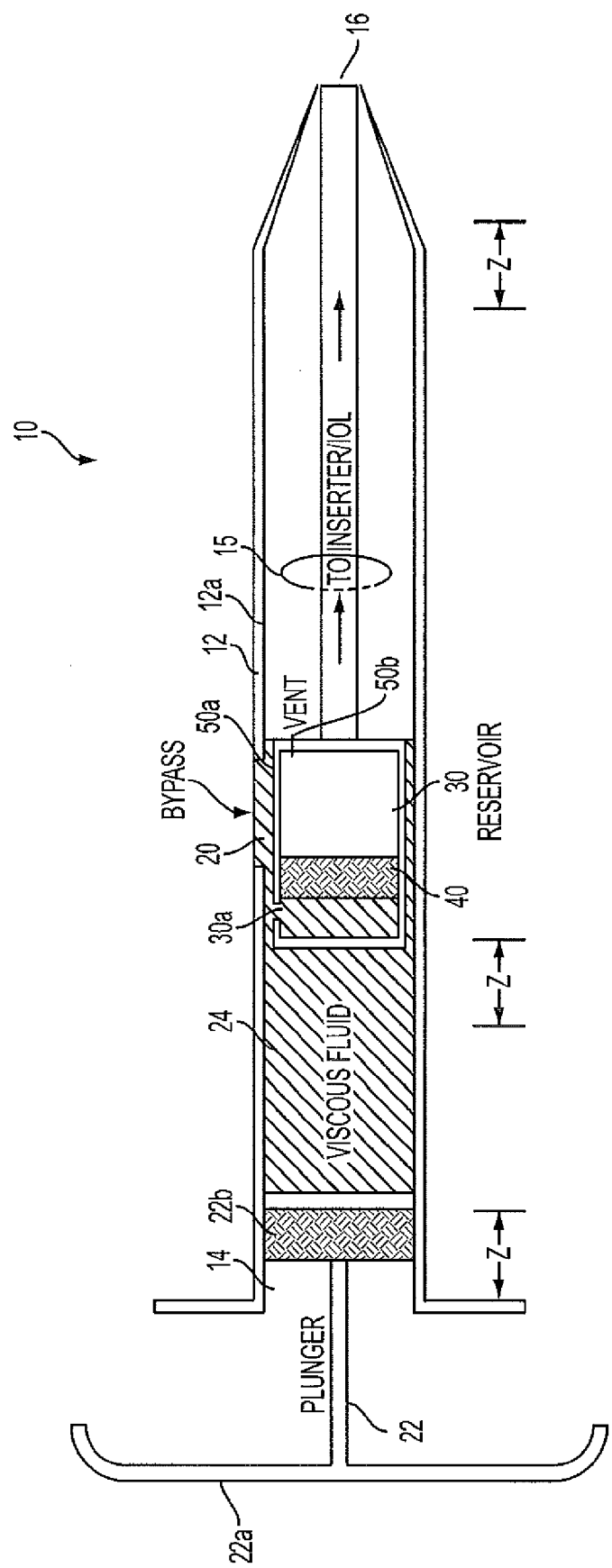
FIG. 1 is a schematic cross-sectional diagram illustrating an embodiment of an IOL inserter according to the present invention.

With reference to the schematic diagram of FIG. 1, a device 10 in accordance with the invention may include a substantially tubular lumen 12, having an open proximal end 14 and opposite distal tip 16, which distal tip 16 may typically be inserted into an incision in an eye for passing an IOL 15 through at least a tapered lower portion of lumen 12, out of inserting tip 16, and into the eye (not shown). IOL 15 may be loaded into lumen 12 through any known IOL loading methodology, e.g., through a chamber opening in the lumen 12 below the reservoir 30.

The tubular lumen 12 may include an inner wall 12a and an outer wall 12b. Inner wall 12a may include a hollowed portion 20 that may be substantially rectangular in shape, and which may be of a sufficient length along the inner wall for affecting, in conjunction with reservoir 30, the decreased displacement pressure upon advanced actuation of plunger 22. Portion 20 geometry may also be tapered, thus allowing for an increasing or decreasing orifice size through which fluid flows as the reservoir travels distally. In other words, the bypass cross sectional area may vary with stroke. The plunger 22 displacement directly displaces the reservoir 30 an equivalent distance until the bypass port is uncovered. When the bypass port is uncovered, fluid escapes the primary chamber through the bypass port and into the reservoir chamber. The main reservoir fluid volume decreases and the reservoir no longer moves linearly in a one-to-one ratio with the plunger. The bypass port may be shaped to increase, decrease or maintain the flow rate or pressure drop through the bypass as the reservoir cylinder wall uncovers various sections of the bypass port.

Plunger 22 may be any known plunger in the available art, and may have an axial length suitable for the purposes discussed herein, although the axial length may generally be less than known plungers due to the decreased stroke needed to expel the IOL 15 in the instant invention. Plunger 22 may have an external portion 22a extending outside of lumen 12, which external portion may allow exertion of pressure thereupon by a user. That is, proximal end 22a of plunger 22 may include a press or flange for advancing the plunger through the longitudinal passageway of the tubular lumen 12 in the manner of a syringe. As such, the proximal end 22a of plunger may be substantially flat or slightly rounded, so as to allow for a user's hand or finger to exert pressure thereon, and/or may include one or more finger loops for receiving a user's finger (s) (not shown). The distal end 22b of plunger 22 may be formed so as to exert a downward pressure on viscous fluid 24 upon advancing of plunger 22. As such, the distal end 22b may be substantially tubular, and of a circumference approximately matching that of inner wall 12a. Distal end 22b may further comprise a gasket or similar device along the outer circumference thereof at least so as to provide a relative seal as between the distal end 22b of plunger and the inner wall 12a.

Reservoir 30 may bleed off the volume of viscous fluid as the plunger 22 is significantly advanced, thus resulting in decreased displacement of the inserter 10 as the plunger nears the end of its stroke. As discussed above, reservoir 30 may include an opening 30a that is proximate to a hollowed portion 20 of inner wall 12a, and that is, in advanced operation, aligned with hollowed portion 20. That is, opening 30a may reside in reservoir 30 longitudinally toward the distal end 16 of lumen 12, such that actuation of plunger 22 does not immediately cause an alignment between opening 30a and hollowed portion 20. However, upon such an alignment, a bypass pathway for viscous fluid 24 is created from the viscous fluid containing portion of lumen 12 (below the distal end 22b of plunger 22 to the top of reservoir 30), up and across hollowed portion 20, and down through opening 30a into reservoir 30. Open portion 30a may be dimensioned with respect to hollowed portion 20, and with respect to the flow rate of viscous fluid 24, so as to allow for a sufficient flow rate of viscous fluid 24 into opening 30a such that the displacement force per plunger stroke is decreased approaching the insertion point as desired in a given application. Open portion 30a may be dimensioned with respect to hollowed portion 20, and with respect to the flow rate of viscous fluid 24, so as to allow for a sufficient flow rate of viscous fluid 24 into reservoir 30 such that the inserter tip 16 displacement per plunger displacement is decreased or increased, and/or linear or variable, approaching the insertion point as desired in a given application.

Viscous fluid 24 may be any known fluid having sufficient viscosity so as to avoid leakage about distal end 22b of plunger 22, and so as to allow for an acceptable flow rate through opening 30a. For example, viscous fluid 24 may be hydraulic fluid and/or a hydrogel. Of course, particularly in medical or surgical applications, it may be preferred that viscous fluid 24 is not harmful in any way to patients in the event of leakage into the IOL chamber and/or into the narrowed portion of lumen 12 through which the IOL passes to injection.

In optional embodiments, float 40 may reside within reservoir 30. Float 40 may respond to entry of viscous fluid 24 through opening 30a by moving, responsively to viscous fluid 24, at a predetermined rate, thereby allowing for further refinement of the flow rate of viscous fluid 24 and hence for further refinement of the decrease in displacement pressure responsively to plunger stroke once viscous fluid begins to flow. In other embodiments, float 40 may be fixed within reservoir 30, so as to limit the amount of viscous fluid 24 that may enter reservoir 30, and hence to limit the amount of force absorption available per plunger stroke. Moreover, float 40 may serve to seal reservoir 30 at an end of reservoir 30 opposite, or substantially opposite, the end of reservoir having opening 30a.

Figure 2:
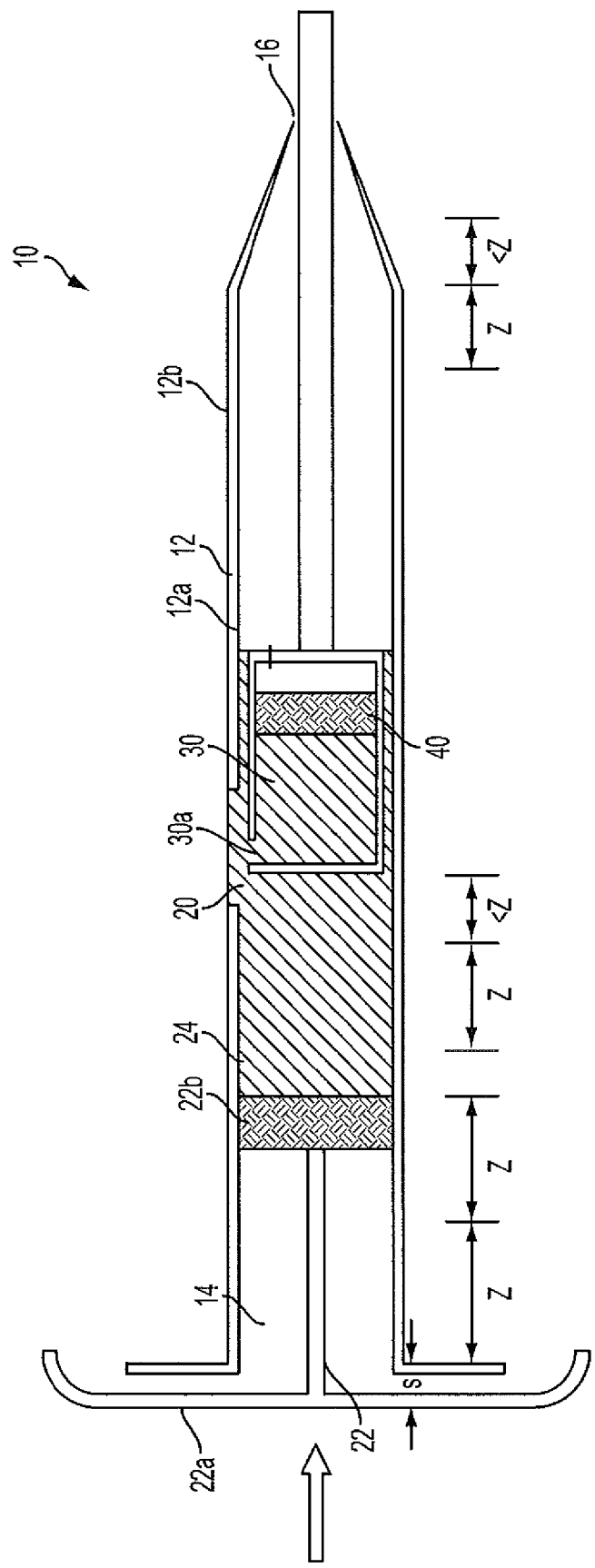
FIG. 2 is a schematic cross-sectional diagram illustrating an embodiment of an IOL inserter according to the present invention.

As discussed above with respect to a plunger position of FIG. 1, for the first distance Z advanced by plunger 22 (as has occurred in FIG. 1), opening 30a has not yet aligned with hollowed portion 20. Thus, as shown, upon exertion of plunger stroke towards insertion of IOL 15, there existed a one-to-one correspondence between the distance traveled by plunger 22 and the distance traveled by reservoir 30 (and hence, there is a one-to-one ratio between the plunger stroke and the inserter stroke). However, and as illustrated in FIG. 2, this one-to-one correspondence may not be maintained. For example, FIG. 2 shows a schematic diagram illustrating a plunger 22 that is well-advanced into lumen 12. In the illustration, once opening 30a in reservoir 30 is advanced sufficiently into alignment with hollowed portion 20, viscous fluid 24 flowed increasingly into reservoir 30, thereby partially "absorbing" the displacement of the plunger stroke. Consequently, in the example shown, the second time that lateral distance Z is advanced by plunger 22 (the first distance Z was travelled in the illustration of FIG. 1) reservoir 30 travels a lateral distance less than (<) Z along lumen 12. Hence, the inserter stroke ratio in this example is less than one to one of the plunger stroke. That is, the position along the plunger stroke at which the reservoir 30 aligns with hollowed portion 20 translates a plunger displacement Z into a displacement of the inverter tip 16 of <Z. As such, although in this illustration the displacement of the inserter tip is varied to be less than that of the plunger, the disclosed embodiments may provide any variable displacement using constant force to the plunger.

In embodiments, the extent of the plunger displacement may vary until the bypass pathway is provided. For example, the bypass pathway may be provided only upon a substantial advance of the plunger a quarter way, i.e., 25%, along the full available plunger stroke; halfway, i.e., 50% along the full available plunger stroke; or three quarter way, i.e., 75% along the full available plunger stroke. It is also envisioned that the bypass pathway may be provided at any point along the lumen to provide the required displacement stroke ratio necessary to achieve a controlled delivery of an IOL.

It will thus be appreciated that the distances shown in FIGS. 1 and 2 are also exemplary only, and the correspondences of the distances in lateral travel to displacement at the inserting tip will be dependent upon numerous factors. These factors include but are not limited to the amount and type of viscous fluid, the size and placement of opening 30a, the length and depth of hollowed portion 20, the length of plunger 22, the presence or absence of float 40, the initial distance between the distal end 22b of plunger 22 and the reservoir 30, and/or the like.

Accordingly, a user of the present IOL inserter may avoid difficulty, as was frequently encountered in the prior art, with the IOL insertion speed, force and stroke, at or near the point of IOL insertion necessary to overcome the counter-pressure caused by driving the IOL for insertion through the narrowing portion of the lumen 12. That is, the user may avoid unintentional "popping" of the IOL into the eye. Thus, the need for secondary surgery, or the need to damage surrounding tissue by adjusting or removing the IOL after insertion may be avoided.

Yet further, a user may have sufficient control at the insertion point through the use of the present invention so as to necessitate the use of only one hand to actuate plunger 22 to insert the IOL, thereby freeing the second hand of the user, typically required in the prior art for a refined insertion, to engage in other activities. Thus, surgical efficiency may be improved. This need for only one hand for plunger actuation is provided, in part, because a constant force asserted by the user on the plunger 22 will result in a lesser insertion displacement force on approaching the end of the plunger stroke. As such, the user will have refined control at the point of insertion through the use of the disclosed embodiments.

In further exemplary embodiments, valving via valve 50*a* or venting via vent 50*b* may at least partially allow for further refined control of the input to output displacement. For example, the bypass pathway may include a valve 50*a* to reduce the flow of viscous fluid 24, thereby allowing increased stroke of the IOL inserter. Moreover, a needle valve or similar valve may be used in line with the bypass to control the amount of fluid that fills the reservoir 30, to therefore increase or decrease the displacement difference in plunger stroke relative to the insertion stroke.

Figure 3:
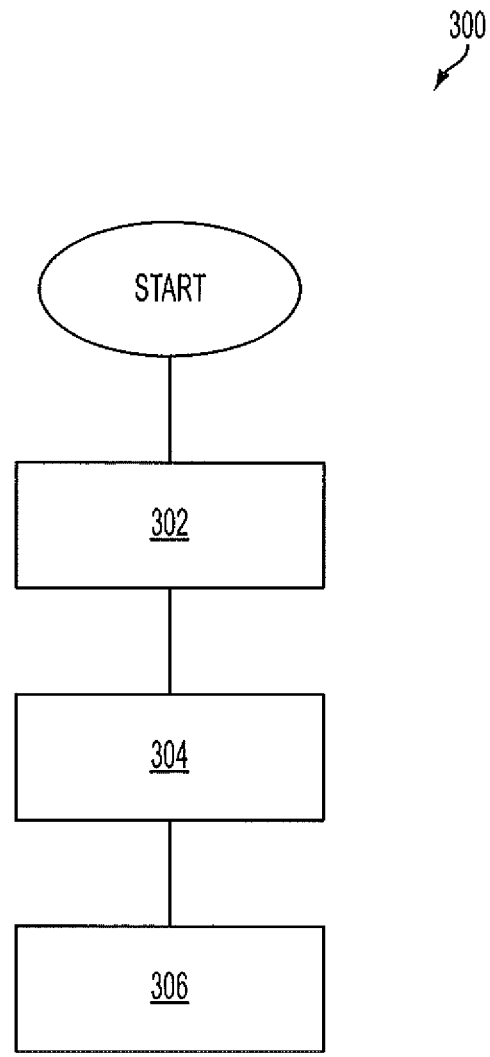
FIG. 3 is a flow diagram illustrating an exemplary method according to the present invention.

FIG. 3 is a flow diagram illustrating a method in accordance with the herein disclosed embodiments. In the illustrative embodiment of FIG. 3, the method 300 may include the step 302 of providing a lumen having inserted therein a plunger, and further having therein a viscous fluid in fluid communication with the distal end of the plunger and with a reservoir. Step 304 includes, at least upon advanced actuation of the plunger, providing a bypass pathway for the viscous fluid such that the displacement of the reservoir (and hence of the IOL insertion) is non-linear with the actuation of the plunger. Step 306 includes providing for the insertion of an IOL upon completion or near-completion of the plunger stroke.

Those skilled in the pertinent arts will appreciate, in light of the discussion herein, that the present invention also has applicability for use in any pharmaceutical, medical, scientific, or food preparation field in which a hypodermic syringe is used. Further, the disclosed embodiments are applicable in the automotive field, such as for hydraulic brake control as between master and slave cylinders.

Those of ordinary skill in the art may recognize that many modifications and variations of the herein disclosed systems and methods may be implemented without departing from the spirit or scope of the invention. Thus, it is intended that the present invention covers such modifications and variations provided they come within the scope the appended claims and their equivalents.

What is claimed is:

1. An inserter suitable for inserting an intraocular lens (IOL), comprising:
   a lumen comprising a longitudinal passageway terminating at an IOL insertion tip suitable for inserting the IOL, and having an inner wall including at least one hollowed portion;
   a plunger for advancing along at least an upper portion of the longitudinal passageway and terminating at a distal plunger end;
   a reservoir within the longitudinal passageway between the distal plunger end and the IOL insertion tip, and having an opening that is misaligned with the at least one hollowed portion prior to advancing of the plunger and that is aligned with the at least one hollowed portion during advancing of the plunger; and
   a viscous fluid within the longitudinal passageway and adjacent to the distal plunger end and to said reservoir, wherein the viscous fluid flows along a bypass formed of the at least one hollowed portion and the opening and into said reservoir,
   wherein the viscous fluid that enters the reservoir is blocked from reaching the IOL insertion tip.

2. The inserter of claim 1, wherein the flow of viscous fluid along the bypass thereby decreases an inserting displacement force effected at the IOL insertion tip from a plunger displacement force applied to said plunger.

3. The inserter of claim 1, wherein the flow of viscous fluid along the bypass thereby increases an inserting displacement force effected at the IOL insertion tip from a plunger displacement force applied to said plunger.

4. The inserter of claim 1, wherein said lumen comprises an open proximal end suitable for receiving said plunger and the IOL insertion tip, with the longitudinal passageway extending therebetween.

5. The inserter of claim 4, said plunger further comprising a plunger shaft having a proximal plunger end external to the open proximal end, the plunger shaft extending into the open proximal end, wherein the proximal plunger end is opposite the distal plunger end along the plunger shaft.

6. The inserter of claim 5, the proximal plunger end comprising a receiver suitable for receiving a hand of a user.

7. The inserter of claim 6, the receiver comprising at least one finger loop.

8. The inserter of claim 1, wherein the longitudinal passageway is tapered proximate to the IOL inserting tip.

9. The inserter of claim 1, further comprising a valve within the bypass for partially controlling a rate of the flow of said viscous fluid.

10. The inserter of claim 1, further comprising a vent integral with said reservoir for partially controlling a rate of the flow of said viscous fluid.

11. The inserter of claim 1, wherein the alignment occurs only in a final half of the advance of said plunger.

12. The inserter of claim 1, wherein the alignment occurs only in a final quarter of the advance of said plunger.

13. The inserter of claim 1, wherein the alignment occurs throughout the entire advancement of said plunger.

14. The inserter of claim 1, further comprising a chamber suitable for receiving the IOL for insertion, said chamber being between said reservoir and the IOL insertion tip along the longitudinal passageway.

15. A system for inserting an intraocular lens through a small incision into an eye, comprising:
   a lumen including a physically separated viscous fluid and a reservoir suitable for receiving the viscous fluid, and an inserting tip; and
   a bypass pathway existent only upon a substantial advance of a plunger longitudinally along said lumen, said bypass pathway allowing a flow of the viscous fluid into the reservoir, thereby decreasing a displacement force effected at the insertion tip from a plunger displacement force applied to the plunger.

16. The system of claim 15, wherein said lumen comprises a tapered longitudinal passageway with the narrowing taper proximate to the inserting tip.

17. The system of claim 15, the plunger comprising a portion external to said lumen having a receiver suitable for receiving a hand of a user.

18. The system of claim 15, further comprising a valve within the bypass pathway for partially controlling a rate of the flow of the viscous fluid.

19. The system of claim 15, further comprising a vent integral with the reservoir for partially controlling a rate of the flow of the viscous fluid.

20. The system of claim 15, wherein the substantial advance comprises an advance of greater than 50%.

* * * * *